United States Patent [19]

Brugger et al.

[11] Patent Number: 4,674,491
[45] Date of Patent: Jun. 23, 1987

[54] INHALER

[75] Inventors: Inge Brugger, Prinz-Karl-Strasse 5a, 8130 Starnberg, Fed. Rep. of Germany; Stephan Brugger, Starnberg, Fed. Rep. of Germany

[73] Assignee: Inge Brugger, Fed. Rep. of Germany

[21] Appl. No.: 764,043

[22] Filed: Aug. 9, 1985

[30] Foreign Application Priority Data

Aug. 9, 1984 [DE] Fed. Rep. of Germany ....... 3429389

[51] Int. Cl.$^4$ ............................................. A61M 11/00
[52] U.S. Cl. .......................... 128/200.14; 128/200.18; 128/203.15; 239/338; 239/526; 239/600
[58] Field of Search ...................... 128/200.14–200.23, 128/203.15, DIG. 26; 222/635, 637; 239/338, 526, 600; 261/30, 78 A, DIG. 65

[56] References Cited

U.S. PATENT DOCUMENTS

| 487,211 | 6/1938 | Curry | 128/200.18 |
| 1,263,079 | 10/1915 | Leon | 128/200.18 |
| 1,642,757 | 3/1923 | Wiechmann | 128/200.21 |
| 3,603,308 | 9/1971 | Spradling | 128/204.25 |

*Primary Examiner*—Henry J. Recla
*Assistant Examiner*—Randy Citrin

*Attorney, Agent, or Firm*—Sughrue, Mion, Zinn, Macpeak, and Seas

[57] ABSTRACT

The invention relates to an inhaler for atomization, dispersing and mixing of fluid or powdery substances by means of a pressurized gas flow (30) for production of an aerosol. The inhaler consists of an atomization head (1) arranged in the upper end of a two part hand grip (2). The atomization head (1) has a central atomization nozzle comprised of a nozzle head (23) and a gas flow controller (27), a connection passage (21) for pressurized gas supply, an air supply chimney (28) and an aerosol outlet passage (28) for connection to a mouthpiece. The nozzle head (23) contains a central pressurized gas passage (22) and lateral suction channels (24,25) for the atomization material (26). According to the invention the atomization head (1) has a spherical shape and is surrounded by correspondingly shaped hollow spherical parts (5,6) of the hand grip. The low height is achieved in that between the container (18) receiving the atomization material (26) and the cap (19), an insert (20) and a deflector (31) on the lower edge of the air supply chimney (28) are provided, by which the aerosol flow produced is guided in a labyrinthine manner via an edge (32) on the deflector (31) and an edge (33) on an insert (20) to the outlet passage (29). In this way, larger particles unsuitable for lung ingestion (extra thoracic) are excluded.

13 Claims, 2 Drawing Figures

INHALER

This invention relates to an inhaler for atomizing, dispersing and mixing of fluid and powdery substances in or with gas by means of a pressurized gas flow for the production of an aerosol, which comprises an atomization head having a central spray head and a connection member for the pressurized gas conduit and an aerosol outlet member for connection to a mouthpiece for the patient.

Such an atomizing device is described in German Pat. No. 927 920. In this device, a gas flow regulator is so arranged in the outlet jet of the pressurized gas flow that its bottom edges contact the sleeve of the gas outlet jet in such manner that the greater part of the gas flow is spread out in the form of a fan on the edges, the feed for the material to be atomized being so arranged beneath the air fan that the material enters into the spread fan and thus thorough mixing of the material to be atomized with the pressurized gas is ensured. Since in practically all cases air is employed as pressurized gas for aerosol therapy, one thus obtains a finely dispersed suspension of the liquid or powdery active substances in air.

If one wishes to employ the known spray either for a new patient or for a different form of aerosol therapy, the spray must first of all be disassembled and thoroughly cleaned before the reservoir for receiving the active substance can be refilled with a new active substance. Such cleaning is time consuming. In many cases it is also necessary to effect repeated treatment on one and the same patient for which then in each case a spray must be refilled with the same active substance. A further known atomizing device is also described in German Pat. No. 11 47 355.

It is therefore the object of the invention to provide an inhaler of the said type which by separation of the components for operation and for the spray enables a simplified replacement of these components, that is to say of the atomization head and the hand grip. The simple construction of the atomization head, its sturdy construction and its simple disassembly for cleaning provides thus a "personal" spray which can be stored in a simple manner away from the hand grip and provided with the active substance for a particular patient and in the event of its reuse can be simply connected to the hand grip and so can be connected to the pressurized gas supply.

By means of the separate construction of hand grip and atomization head, the hand grip can also be constructed in a more ergonomically favourable manner than is the case in the known atomization device, where the housing wall of the spray was simply used as the hand grip. The simple replaceability of the atomization head suggests the use of the same hand grip for plurality of atomization heads, whereby no operational time is lost during cleaning of the atomization heads so long as sufficient atomization heads are available.

These objects are achieved with an inhaler of the type defined in the introduction which is charaterized in that it comprises a hand grip having two hollow parts embracing the atomization head, the two parts being connected together at the lower end of the grip part by means of a film hinge, and in that the atomization head comprises a somewhat spherical configuration adapted to the hollow parts of the grip part.

Further advantageous embodiments of the inhaler according to the invention appear in the sub-claims.

For explanation of the new inhaler, reference may be made to the accompanying drawing in which.

Figure 1:
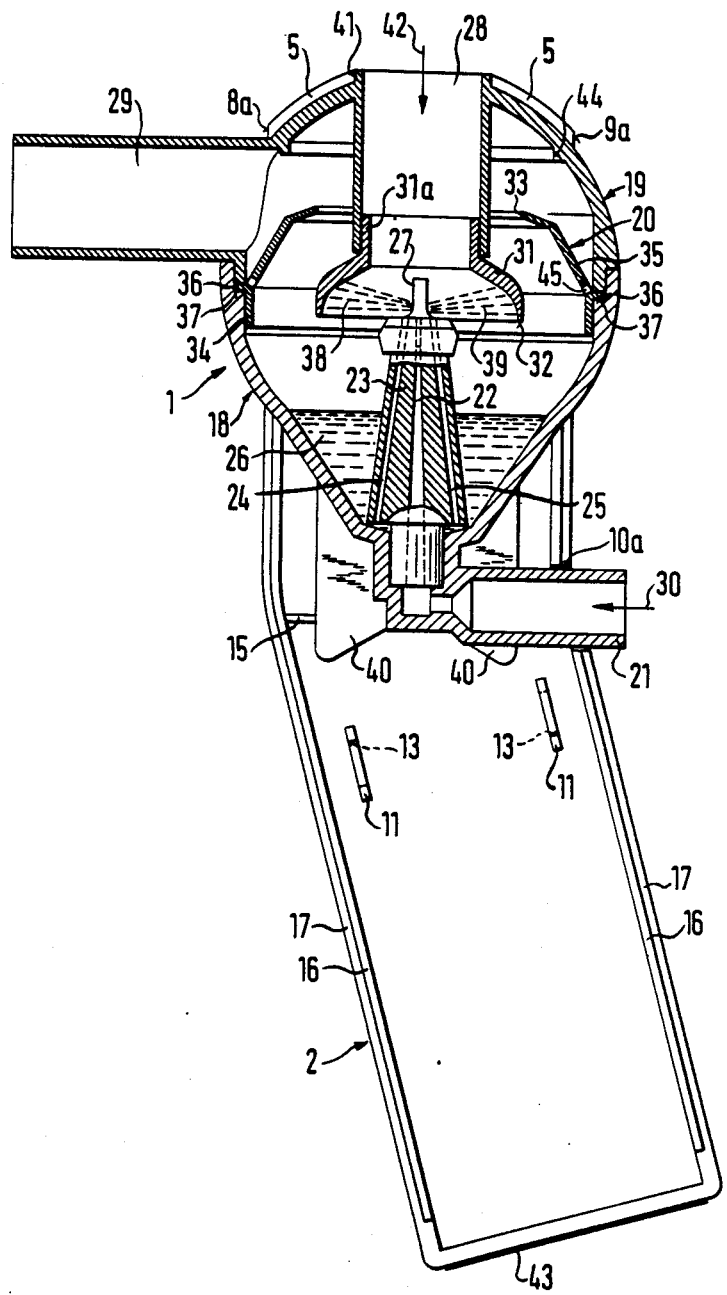
FIG. 1 shows a central longitudinal section through the new inhaler.

As can be seen from FIG. 1, the inhaler consists essentially of the atomization head 1 which is located in the upper region of the hand grip 2.

Figure 2:
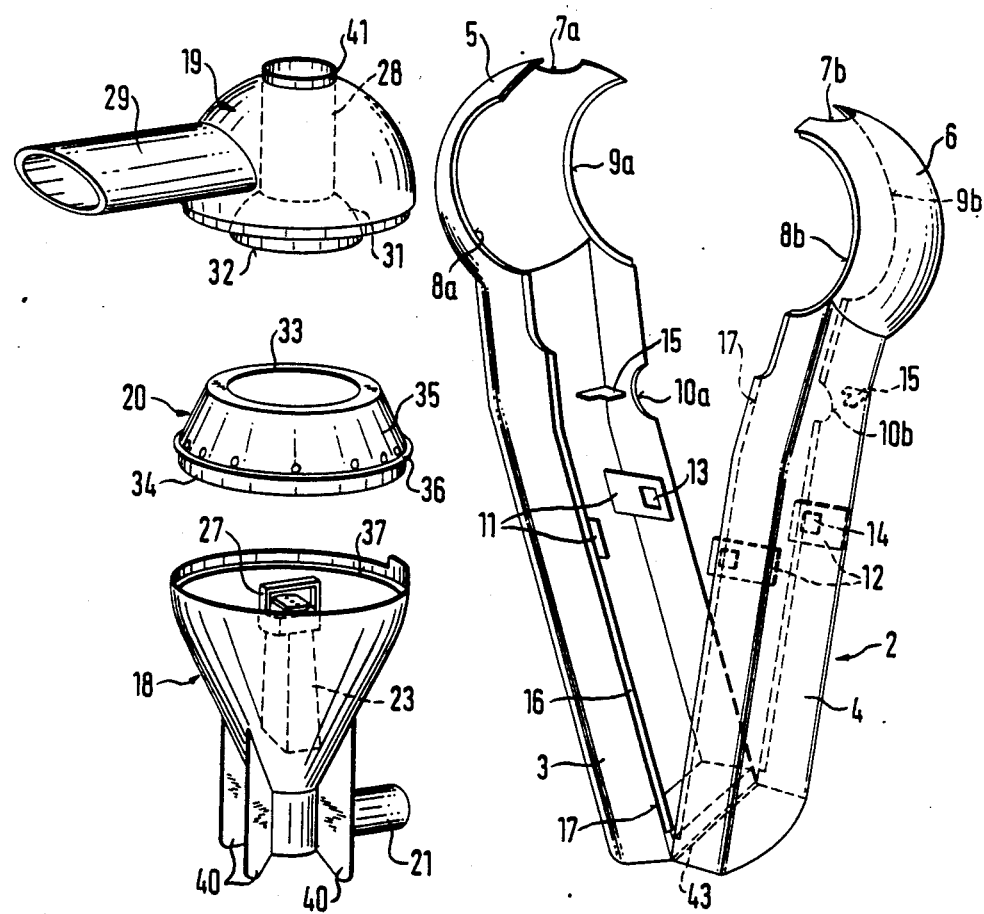
FIG. 2 shows a perspective view of the individual parts of the inhaler according to FIG. 1, the hand grip being illustrated in its opened position and the essential parts of the atomization head being illustrated in a disassembled condition left of the hand grip.

Hand grip 2 consists, as may be seen best from the righthand illustration in FIG. 2, of a hollow lefthand grip part 3 and hollow righthand grip part 4 which are connected together by means of a film hinge 43 at the lower end of the grip region. The hollow grip parts 3 and 4, somewhat rectangular in cross-section, are constructed in their upper region as hollow spherical halves 5 and 6 which are connected to the grip region. The grip region can be slightly angled in an egonomically favourable form in order to permit a non-tiring hand position of the right operating hand for the user during inhaling. For this purpose, the grip parts are slightly angled approximately in the region of the opening halves 10a, 10b for the emergence of the connection member 21 for the pressurized gas 30, as may be seen from FIG. 1. The two opening halves 7a, 7b on the head of the two hollows spherical parts 5, 6 serve to receive the cylindrical chimney extension 41 on the upper end of the coaxial air supply chimney 28, whilst the opening halves 8a, 8b carry the aerosol outlet pipe 29 of the cap 19 of the atomization head 1 and the opening halves 9a, 9b to the rear of Fig. 2 and lying opposite the opening halves 8a, 8b permit passage of the rear spherical section of the atomization head 1 lying opposite the aerosol outlet pipe 29. The opening halves 10a, 10b embrace the connection pipe 21 which can be connected to the pressurized gas supply with the intermediary of an interruption valve which may be simply operated by hand and is not shown in the drawing.

In each of the hollow grip parts are located two latching ears; in the left grip part these are the latching ears 11 with corresponding opening 13 for receiving the projections 14 which are located on the latching ears 12 in the righthand grip part. Mutually correct positioning of the two grip parts of the hand grip 2 is aided furthermore by the construction of peripheral ridges 16 on the edges of the grip part 3 and complementary surfaces 17 cooperating with these on the edges of the opposing grip part 4. Flanges 15 extend upwardly from the grip parts 3 and 4, and engage the ribs 40 on the base portion 14 to secure the container 18 within the hand grip 2.

The atomization head 1 comprises altogether six components of which in the exploded view of FIG. 2 on the left only three parts are illustrated, that is to say the container 18 with the four positioning ribs 40 which serve in addition for the mounting of the container 18 removed from the grip parts 3, 4, the inserts 20 and the cap 19 with the outlet pipe 29 for the aerosol. In the cap 19 are integrated the coaxial chimney 28 and the aerosol outlet part 29. The coaxial chimney 28 is made cylindrical whilst the outlet pipe, as may be seen from the perspective view in FIG. 2, has a somewhat elliptical cross-section. The deflector 31 is in FIG. 2 secured in the cylindrical chimney 28. The air supply chimney 28 can also be constructed in one piece with the deflector 31; the two part construction however simplifies cleaning after use.

The container part consists of three parts: the container 18 itself, the nozzle head 23 which is mounted in the container and which is mounted with its cylindrical foot part in the lower end of the container 18, and the gas flow control 27 which is mounted on the nozzle head 23. The three parts represented to the left of FIG. 2 in exploded view may be slid together axially and so assembled. In this connection, the insert 20 engages with its cylindrical peripheral flange 34 in the container 18 where it lies with the flange 36 on the annular shoulder 37 on the upper edge of the container 18. Finally, the cap 19 is mounted on the container 18 with insert 20 whereby the spherical, somewhat egg-shaped configuration illustrates in FIG. 1 results. The thus constructed atomization head forms an autonomous component which can be removed and supported on the ribs 40 as feet (without hand grip 2).

The short compact construction of the atomization head 1 is achieved in that the constructional height of the coaxial air supply chimney 28 is shortened by arranging baffle plates for the aerosol between the location of its formation and the aerosol outlet pipe. These baffle plates are first of all the deflector 31 on the lower end of the chimney 28. The deflector 31 is slid into the air supply chimney 28 from below by means of the cylindrical extension 31a. It can optionally also be constructed in one piece with the air supply chimney. The aerosol zones 38 and 39 formed on the deflection surfaces of the gas flow control 27 interact with the inner wall of the bell-shaped deflector 31, larger aerosol particles being further reduced on this wall and being transformed into the desired range of particle size of about 0.5 to 5 microns. Larger drops are extracted on the edge 32 of the deflector 31. They drop back from the edge 32 into the atomization supply 26 in the container 18. On its subsequent path, the aerosol flow must pass around the edge 32 between the air supply chimney 28 and insert 20 and thus skirt a second edge, that is to say the edge 33 of the insert 20 where further drops of too large a size are removed and flow away on the inner wall of the wall part 35 and so pass back to the atomization material 26 on the floor of the container 18.

In this manner it is possible to produce an aerosol spray suitable for the lungs with a relatively small construction of the atomizer 1, which aerosol is to a large part at the desired particle size when it escapes from the outlet part 29 and supplied to the patient.

The mode of operation for the production of the aerosol is known. In connection with FIG. 1 it may be pointed out that the gas entering in the direction of the arrow 30 into the connection pipe 21 can be controlled by means of an outer valve not illustrated in the drawing in sychronism with the breathing of the patient. This pressurized gas reaches the central suction channel 22 which tapers in its upper region to a narrow outlet nozzle. As a result of the high gas velocity in this region, the matrial 26 to be atomized is sucked from the lateral suction channels 24, 25 and accelerated against the deflection surfaces of the gas flow control 27 lying opposite the discharge opening of the nozzle head 23. On the inclined deflection surfaces of the gas flow control 27, the two lateral aerosol branches are produced whose particle spectrum is improved by the further intensive impact on the inner wall of the neighbouring deflector 31 to produce an aerosol which is more favourable for lung ingestion.

The edge 32 on the deflector 31 and the edge 33 on the insert 20 therefore cooperate in the described manner as additional filters for improving the particle spectrum. Particles which are too large are removed from the aerosol spray and flow back to the atomization material 26 in the container 18. In the same manner, also the drip edge 44 improves the filtering effect of the edges 32 and 33 and excludes larger particles from the aerosol stream before these leave the inhaler through the outlet pipe 29. In order to ensure that the liquid directed away by the drip edge 44 can also flow back again to the atomization supply 26, opening 45 are provided in the lower region of the spherical wall part 35 of the cap 20.

Although the known compressor driven inhaler device according to DE-PS No. 1 147 355 has also compared relatively well in the past with tested devices of similar construction of other manufacturers (c.f. the journal of the Goods Testing Institute June 1983 pages 32 to 37, particular page 36), the intrathoracic aerosol proportion particularly important for aerosol therapy could be increased with the inhaler of the invention by considerably more than 50% inspite of its small constructional height compared with the usual therapy devices. In this connection, the medicinal examination was carried out according to the same method as described in the mentioned journal.

The manufacture of the inhaler in injection molding technique from a suitable synthetic material also permits cheap manufacture of the atomization head by the injection molding method. Such a head can therefore also be used as a one-way head or a throw-way head, the time consuming cleaning when using the spray sequentially with various patients or with differing medications being avoided.

Of course, the atomization head can also be cleaned and stored for repeated use.

A preferred field of use for the inhaler is presented by the treatment of inpatients or outpatients with aerosol therapy repeated for example on a daily basis; in such a case, the atomization head with the reservoir is simply removed from the hand grip after therapy, provided with a name plate for identification and placed in a suitable location until the next therapy.

We claim:

1. Inhaler for atomizing, dispersing and mixing of fluid and powdery substances in or with gas by means of a pressurized gas flow for producing an aerosol, comprising:
    an atomization head (1) comprising housing means forming a hollow chamber for receiving the material to be atomized, a connection passage (21) extending into said chamber adapted to be connected to a pressurized gas supply, an aerosol outlet passage (29) extending from said chamber for connection to a mouthpiece for a patient, and a central nozzle head means communicating with said connection passage and extending into said chamber for atomizing and directing a mixture of the atomization material and pressurized gas to said outlet passage; wherein
    the inhaler has a hollow two part handgrip (2) having an upper end with a complementary configuration to said housing, the two parts being connected together at lower ends thereof by means of a film hinge (43), the atomization head having a somewhat spherical configuration, and the hand grip having means for releasably maintaining the two parts secured around the atomization head.

2. Inhaler according to claim 1, wherein the housing comprises a container (18) with a base portion having ribs (40) extending laterally therefrom, and the handgrip parts have flanges (15) extending inwardly therefrom and positioned such that the flanges on the grip parts engage the ribs on the base portion whereby the container is held securely in the hand grip.

3. Inhaler according to claim 2, wherein the means for releasably maintaining the two grip parts secured comprise latching ears (11, 12) having openings (13) located in the interior of one grip part and latching ears (12) having projections (14) in the other grip part, wherein the openings of the latching ears in one grip part cooperate with corresponding projections of the latching ears of the other grip part.

4. Inhaler according to claim 1, further comprising: an air inlet chimney disposed above said nozzle head;
recesses (7a, 7b) provided on the upper end of the hand grip for receiving an extension (41) of the air inlet chimney; and
recesses (10a, 10b) provided on the hand grip for receiving the connection passage.

5. Inhaler according to claim 1, further comprising:
the hollow grip parts of the hand grip each having U-shaped cross-sections defining oppositely facing channels, and peripheral edges of each channel mutually engaging each other, the peripheral edge of one part having a peripheral flange (16) and the peripheral edge of the other part having a cooperating peripheral groove (17), said peripheral flange mating with said opposite peripheral groove when said grip parts are secured together.

6. Inhaler according to claim 1, wherein the nozzle head means has a gas flow control means (27) for dispersing the mixture in said housing means and the housing comprises a container (18) for receiving the material to be atomized and a cap (19) mounted on said container having an air inlet chimney (28) having one end extending into said chamber and terminating above said nozzle head means, an opposite end extending through said cap and communicating with external atmosphere, and an inwardly extending intermediately arranged insert (20) cooperating with said chimney to define a tortuous flow path from said nozzle head means to said outlet passage.

7. Inhaler according to claim 6, wherein the air supply chimney is coaxially arranged and constructed in one piece with the cap.

8. Inhaler according to claim 6, further comprising:
a deflector (31) having a cylindrical extension (31a) at one end which is fitted into the inner diameter of said one end of said chimney.

9. Inhaler according to claim 8, wherein the deflector is a downwardly and outwardly bell-shaped member which extends outwardly in a sperical or parabolic shape and diminishes the free annular space in the atomization head for the ascent of the aerosol.

10. Inhaler according to claim 9, wherein the nozzle head means terminates in a horizontal surface and the deflector extends downwardly and terminates in a peripheral edge which lies in the same plane as the horizontal surface of the nozzle head means.

11. Inhaler according to claim 6, wherein the insert has a conical wall part (35) which extends from the inner wall of said container inwardly and terminates in an upper edge (33) surrounding said chimney and delimits a further annular space with the outer surface of the air supply chimney through which the aerosol is conducted into the outlet passage.

12. Inhaler according to claim 11, wherein said conical wall part of said insert has at least one hole (45) adjacent the container wall for return of atomization material thereto and an annular drip edge (32) is formed on the inner wall of the cap above said insert and which drip edge cooperates with the edge on the insert in such a manner that in the thus-formed deflection position larger drops are separated from the aerosol flow and are returned into the atomization material in the container via said hole.

13. Inhaler according to claim 6, wherein said container includes an upper edge having an annular shoulder (37) and said insert includes an annular peripheral flange (36) abutting said shoulder.

* * * * *